United States Patent
Pasquier et al.

(10) Patent No.: US 7,291,183 B2
(45) Date of Patent: Nov. 6, 2007

(54) AGENT AND METHOD FOR DYEING KERATIN FIBERS

(75) Inventors: Cécile Pasquier, Marly (DE); Vèronique Buclin, Morlon (CH); Caroline Kiener, Marly (CH); Anita Roulin, Villarlod (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 328 days.

(21) Appl. No.: 10/529,978

(22) PCT Filed: Feb. 3, 2004

(86) PCT No.: PCT/EP2004/000961

§ 371 (c)(1),
(2), (4) Date: Mar. 24, 2005

(87) PCT Pub. No.: WO2004/078153

PCT Pub. Date: Sep. 16, 2004

(65) Prior Publication Data

US 2006/0010616 A1    Jan. 19, 2006

(30) Foreign Application Priority Data

Mar. 5, 2003    (DE) ................................ 103 09 523

(51) Int. Cl.
*A61K 7/13* (2006.01)
(52) U.S. Cl. ...................... 8/405; 8/406; 8/408; 8/409; 8/573; 8/575; 8/576; 548/146
(58) Field of Classification Search ................ 8/405, 8/406, 408, 409, 573, 575, 576; 548/146
See application file for complete search history.

(56) References Cited

U.S. PATENT DOCUMENTS 3,634,013 A * 1/1972 Maul et al. ..................... 8/409
2004/0060124 A1    4/2004 Pasquier et al.

FOREIGN PATENT DOCUMENTS

| DE | 1 049 381 | 1/1959 |
| DE | 23 34 738 | 1/1975 |
| DE | 101 55 907 A1 | 5/2003 |
| EP | 0 664 114 A1 | 7/1995 |

OTHER PUBLICATIONS

STIC Search Report dated Mar. 30, 2007.*
Vorschrift in Research Disclosure, Oct. 1978, pp. 42-44, No. 17434.

* cited by examiner

*Primary Examiner*—Eisa Elhilo
(74) *Attorney, Agent, or Firm*—Michael J. Striker

(57) ABSTRACT

The object of the present patent application is an agent for coloring keratin fibers based on oxidative dyes and which contains as developer at least one heterocyclic hydrazone derivative of formula (I) (with X=S or O) and as oxidant at least one persulfate salt, further objects being a multicomponent kit and a method for coloring keratin fibers by use of said agent

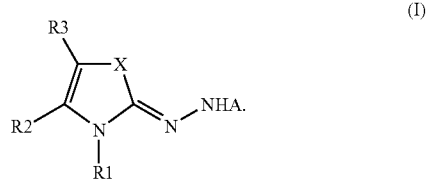

(I)

13 Claims, No Drawings

AGENT AND METHOD FOR DYEING KERATIN FIBERS

CROSS-REFERENCE

The present invention is related to the subject matter of co-pending U.S. patent application Ser. No. 10/530,065. The invention described and claimed hereinbelow is also described in PCT/EP 2004/000961, filed Feb. 3, 2004 and DE 103 09 523.3, filed Mar. 3, 2003. This German Patent Application, whose subject matter is incorporated here by reference, provides the basis for a claim of priority of invention under 35 U.S.C. 119 (a)-(d).

BACKGROUND OF THE INVENTION

The present invention has for an object an agent for the coloring of keratin fibers, for example silk, wool or hair and particularly human hair, based on oxidative dyes and containing at least one heterocyclic hydrazone derivative (of the thiazole or oxazole family) as developer and at least one persulfate salt as oxidant, a multicomponent kit and a method for the coloring of keratin fibers by use of said agent.

Hair colorants are divided mainly into the groups of oxidative colorants or of tinting agents, depending on the initial color of the hair to be dyed and on the end result desired. Oxidative colorants are eminently suited for covering larger gray portions. The oxidative colorants used for an up to 50% portion of gray hair are as a rule referred to as oxidative tinting agents, whereas the oxidative colorants used for a greater than 50% portion of gray hair or for "brightening" are usually referred to as oxidative dyes. Direct dyes are contained mainly in non-oxidative colorants (known as tinting agents). Because of their small [molecular] size, some direct dyes, for example the nitro dyes, can penetrate into the hair and dye the hair directly, at least in the outer regions. Such tinting agents are very gentle to the hair and, as a rule, withstand 6 to 8 hair washes. Direct dyes are also often used in oxidative colorants to create certain shades or for color intensification. The previously known colorant systems, however, cannot meet in every respect the requirements placed on colorants, particularly in terms of luster and color intensity.

Surprisingly, we have now found that heterocyclic hydrazones of the thiazole or oxazole family give with common couplers, for example aromatic hydroxyl and/or amino groups-containing compounds, in the presence of persulfate salts intense colorations in the yellow to blue color range. These novel colorants give unusually brilliant and intense colorations showing very high perspiration resistance.

SUMMARY OF THE INVENTION

The present invention therefore has for an object an agent for the coloring of keratin fibers (A), for example wool, silk, or hair and particularly human hair, characterized in that it contains (a) at least one hydrazone derivative of formula (I) or a physiologically compatible salt thereof

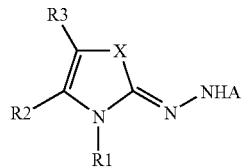

wherein

X denotes oxygen or sulfur;

A denotes hydrogen, an acetyl group, a trifluoroacetyl group, a formyl group, a $(C_1-C_6)$-alkylsulfonyl group or an arylsulfonyl group;

R1 denotes a saturated or unsaturated $(C_1-C_{12})$-alkyl group, a halogen (F, Cl, Br, I)-substituted $(C_1-C_{12})$-alkyl group, a hydroxy-$(C_1-C_{12})$-alkyl group, an amino-$(C_1-C_{12})$-alkyl group, a sulfonic acid-$(C_1-C_{12})$-alkyl group, a formyl group, a C(O)—$(C_1-C_{12})$-alkyl group, a C(O)-phenyl group, a C(O)NH—$(C_1-C_{12})$-alkyl group, a C(O)NH-phenyl group, a substituted or unsubstituted phenyl group or a benzyl group;

R2 and R3 can be equal or different and independently of each other denote hydrogen, a halogen atom (F, Cl, Br, I), a saturated or unsaturated $(C_1-C_{12})$-alkyl group, a halogen (F, Cl, Br, I)-substituted $(C_1-C_{12})$-alkyl group, a hydroxy-$(C_1-C_{12})$-alkyl group, a $(C_1-C_{12})$-alkoxy group, a cyano group, a nitro group, an amino group, a $(C_1-C_{12})$-alkylamino group, a $(C_1-C_{12})$-dialkylamino group, a carboxylic acid, a C(O)O—$(C_1-C_{12})$-alkyl group, a substituted or unsubstituted C(O)O-phenyl group, a substituted or unsubstituted phenyl group or a naphthyl group;

or R2 and R3 together with the remainder of the molecule form a heterocyclic or carbocyclic, saturated or unsaturated, substituted or unsubstituted ring system;

(b) at least one known coupler or a physiologically compatible salt thereof; and (c) a persulfate salt as oxidant.

Depending on the pH of the agent, the compound of formula (I) can also be in equilibrium with the compound of formula (I'):

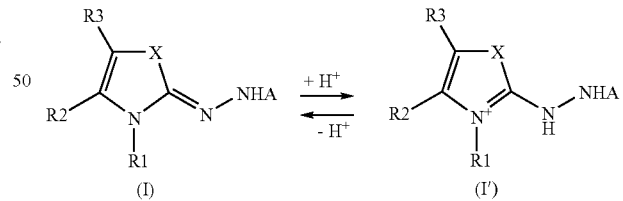

DETAILED DESCRIPTION OF THE PREFERRED EMBODIMENTS

Preferred are hydrazone derivatives of formula (I) or the physiologically compatible salts thereof wherein X denotes sulfur and A stands for hydrogen. Particularly preferred are hydrazone derivatives of formula (I) or the physiologically compatible salts thereof wherein X denotes sulfur, A stands for hydrogen, R1 denotes a saturated or unsaturated $(C_1-C_{12})$-alkyl group, a hydroxy-$(C_1-C_{12})$-alkyl group, an amino-$(C_1-C_{12})$-alkyl group, or a substituted or unsubstituted phenyl group, and R2 and R3 independently of each other denote hydrogen, a saturated or unsaturated $(C_1-C_{12})$-alkyl group, a cyano group, a nitro group, an amino group, a $(C_1-C_{12})$-alkylamino group, a $(C_1-C_{12})$-dialkylamino group, a $C(O)O-(C_1-C_{12})$-alkyl group or a substituted or unsubstituted phenyl group or a naphthyl group, or R2 and R3 together with the remainder of the molecule form a carbocyclic, unsaturated, substituted or unsubstituted ring system.

Following are examples of compounds of formula (I):
3-methyl-2(3H)-thiazolone hydrazone,
3,4-dimethyl-2(3H)-thiazolone hydrazone,
4-tert.butyl-3-methyl-2(3H)-thiazolone hydrazone,
3-methyl-4-phenyl-2(3H)-thiazolone hydrazone,
3-methyl-4-(4-tolyl)-2(3H)-thiazolone hydrazone,
4-(4-methoxy)phenyl-3-methyl-2(3H)-thiazolone hydrazone,
4-(4-ethoxy)phenyl-3-methyl-2(3H)-thiazolone hydrazone,
4-(4-bromophenyl)-3-methyl-2(3H)-thiazolone hydrazone,
4-(3-bromophenyl)-3-methyl-2(3H)-thiazolone hydrazone,
4-(4-chlorophenyl)-3-methyl-2(3H)-thiazolone hydrazone,
4-(3-chlorophenyl)-3-methyl-2(3H)-thiazolone hydrazone,
3-methyl-4-(4-nitrophenyl)-2(3H)-thiazolone hydrazone,
3-methyl-4-(3-nitrophenyl)-2(3H)-thiazolone hydrazone,
4-[(1,1'-biphenyl)-4-yl]-3-methyl-2(3H)-thiazolone hydrazone,
3-methyl-4-(2-naphthalenyl)-2(3H)-thiazolone hydrazone,
ethyl 2-hydrazono-2,3-dihydro-3-methyl-4-thiazolecarboxylate,
3,4,5-trimethyl-2(3H)-thiazolone hydrazone,
3,4-dimethyl-5-phenyl-2(3H)-thiazolone hydrazone,
3,5-dimethyl-4-phenyl-2(3H)-thiazolone hydrazone,
3-methyl-4,5-diphenyl-2(3H)-thiazolone hydrazone,
5-ethyl-3-methyl-4-phenyl-2(3H)-thiazolone hydrazone,
4-(4-bromophenyl)-3-methyl-5-phenyl-2(3H)-thiazolone hydrazone,
3-methyl-5-phenyl-4-(4-tolyl)-2(3H)-thiazolone hydrazone,
5-(4-chlorophenyl)-4-phenyl-3-methyl-2(3H)-thiazolone hydrazone,
5-(4-chlorophenyl)-4-(4-methoxyphenyl)-3-methyl-2(3H)-thiazolone hydrazone,
ethyl 2-hydrazono-2,3-dihydro-3,4-dimethyl-4-thiazolecarboxylate,
4-amino-2-hydrazono-2,3-dihydro-3-methyl-5-thiazolecarbonitrile,
3-ethyl-4,5-dimethyl-2(3H)-thiazolone hydrazone,
ethyl 2-hydrazono-2,3-dihydro-3-ethyl-4-methylthiazolecarboxylate,
5-methyl-3-(1-methylethyl)-4-phenyl-2(3H)-thiazolone hydrazone,
4,5-dimethyl-3-(1-methylethyl)-2(3H)-thiazolone hydrazone,
3-(1-methylethyl)-4,5-diphenyl-2(3H)-thiazolone hydrazone,
4,5-dimethyl-3-propyl-2(3H)-thiazolone hydrazone,
4,5-diphenyl-3-propyl-2(3H)-thiazolone hydrazone,
3-butyl-4,5-diphenyl-2(3H)-thiazolone hydrazone,
4,5-dimethyl-3-(2-methylpropyl)-2(3H)-thiazolone hydrazone,
3-(2-methylpropyl)-4,5-diphenyl-2(3H)-thiazolone hydrazone,
3-hydroxyethyl-2(3H)-thiazolone hydrazone,
3-hydroxyethyl-4-methyl-2(3H)-thiazolone hydrazone,
3-hydroxyethyl-4,5-dimethyl-2(3H)-thiazolone hydrazone,
3-aminoethyl-2(3H)-thiazolone hydrazone,
3-aminoethyl-4-methyl-2(3H)-thiazolone hydrazone,
3-aminoethyl-4,5-dimethyl-2(3H)-thiazolone hydrazone,
3,4-diphenyl-2(3H)-thiazolone hydrazone,
4-methyl-3-phenyl-2(3H)-thiazolone hydrazone,
4-p-biphenylyl-3-phenyl-2(3H)-thiazolone hydrazone,
4-(4-methoxy)phenyl-3-phenyl-2(3H)-thiazolone hydrazone,
4-tert.butyl-3-phenyl-2(3H)-thiazolone hydrazone,
4,5-dimethyl-3-phenyl-2(3H)-thiazolone hydrazone,
5-methyl-3,4-diphenyl-2(3H)-thiazolone hydrazone,
3,4,5-triphenyl-2(3H)-thiazolone hydrazone,
4,5-dimethyl-3-(phenylmethyl)-2(3H)-thiazolone hydrazone,
3-(2-propenyl)-2(3H)-thiazolone hydrazone,
4-methyl-3-(2-propenyl)-2(3H)-thiazolone hydrazone,
4-tert.butyl-3-(2-propenyl)-2(3H)-thiazolone hydrazone,
4-phenyl-3-(2-propenyl)-2(3H)-thiazolone hydrazone,
4,5-dimethyl-3-(2-propenyl)-2(3H)-thiazolone hydrazone,
4,5-diphenyl-3-(2-propenyl)-2(3H)-thiazolone hydrazone,
ethyl 2-hydrazono-2,3-dihydro-3-[(phenylamino)carbonyl]-4-methylthiazolecarboxylate,
3-methyl-4,5,6,7-tetrahydro-2(3H)-benzothiazolone hydrazone,
3-methyl-2(3H)-benzothiazolone hydrazone,
3,6-dimethyl-2(3H)-benzothiazolone hydrazone,
6-chloro-3-methyl-2(3H)-benzothiazolone hydrazone,
7-chloro-3-methyl-2(3H)-benzothiazolone hydrazone,
6-hydroxy-3-methyl-2(3H)-benzothiazolone hydrazone,
5-methoxy-3-methyl-2(3H)-benzothiazolone hydrazone,
7-methoxy-3-methyl-2(3H)-benzothiazolone hydrazone,
5,6-dimethoxy-3-methyl-2(3H)-benzothiazolone hydrazone,
5-ethoxy-3-methyl-2(3H)-benzothiazolone hydrazone,
6-ethoxy-3-methyl-2(3H)-benzothiazolone hydrazone,
3-methyl-5-nitro-2(3H)-benzothiazolone hydrazone,
3-methyl-6-nitro-2(3H)-benzothiazolone hydrazone,
5-acetamido-3-methyl-2(3H)-benzothiazolone hydrazone,
6-acetamido-3-methyl-2(3H)-benzothiazolone hydrazone,
5-anilino-3-methyl-2(3H)-benzothiazolone hydrazone,
6-anilino-3-methyl-2(3H)-benzothiazolone hydrazone,
2-hydrazono-2,3-dihydro-3-methyl-6-benzothiazolecarboxylic acid,
2-hydrazono-2,3-dihydro-3-methyl-4-benzothiazolesulfonic acid,
2-hydrazono-2,3-dihydro-3-methyl-5-benzothiazolesulfonic acid,
2-hydrazono-2,3-dihydro-3-methyl-6-benzothiazolesulfonic acid,
2-hydrazono-2,3-dihydro-3-methyl-7-benzothiazolesulfonic acid,
2-hydrazono-2,3-dihydro-N,N,3-trimethyl-6-benzothiazolesulfonamide,
[(2-hydrazono-2,3-dihydro-3-methyl-6-benzothiazolyl)oxy]acetohydrazide,
3-methylnaphtho[2,3-d]thiazole-2(3H)-one hydrazone,
3-ethyl-2(3H)-benzothiazolone hydrazone,
6-ethoxy-3-ethyl-2(3H)-benzothiazolone hydrazone,
3-propyl-2(3H)-benzothiazolone hydrazone,
3-butyl-2(3H)-benzothiazolone hydrazone,
3-hexyl-2(3H)-benzothiazolone hydrazone,
3-hydroxyethyl-2(3H)-benzothiazolone hydrazone,
3-aminoethyl-2(3H)-benzothiazolone hydrazone,
3-p-methylbenzyl-2(3H)-benzothiazolone hydrazone,
2-hydrazono-2,3-dihydro-3-(2-hydroxyethyl)-6-benzothiazolecarboxylic acid,
2-hydrazono-2,3-dihydro-6-methoxy-3(2H)-benzothiazolepropanesulfonic acid,
6-hexadecyloxy-2-hydrazono-3(2H)-benzothiazolepropanesulfonic acid, ethyl 2-keto-3-benzothiazoline acetate hydrazone,
3-acetyl-2(3H)-benzothiazolone hydrazone,
2-hydrazono-3(2H)-benzothiazole carboxaldehyde,
3-methyl-2(3H)-oxazolone hydrazone,
3-phenyl-2(3H)-oxazolone hydrazone,
3-methyl-2(3H)-benzoxazolone hydrazone,
3-phenyl-2(3H)-benzoxazolone hydrazone,
N-acetyl-3-methyl-2(3H)-thiazolone hydrazone,
N-acetyl-3,4-dimethyl-2(3H)-thiazolone hydrazone,
N-acetyl-3-methyl-4-phenyl-2(3H)-thiazolone hydrazone,
N-acetyl-4-(4-methoxy)phenyl-3-methyl-2(3H)-thiazolone hydrazone,
N-acetyl-3-methyl-4-(4-nitrophenyl-2(3H)-thiazolone hydrazone,
N-acetyl-4-[(1,1'-biphenyl)4-yl]-3-methyl-2(3H)-thiazolone hydrazone
N-acetyl-3-methyl-4-(2-naphthalenyl)-2(3H)-thiazolone hydrazone
ethyl N-acetyl-2-hydrazono-2,3-dihydro-3-methyl-4-thiazolecarboxylate
N-acetyl-3,4,5-trimethyl-2(3H)-thiazolone hydrazone,
N-acetyl-3,4,-dimethyl-5-phenyl-2(3H)-thiazolone hydrazone,
N-acetyl-3,5,-dimethyl-4-phenyl-2(3H)-thiazolone hydrazone,
N-acetyl-3-methyl-4,5-diphenyl-2(3H)-thiazolone hydrazone,
N-acetyl-3-ethyl-4,5-dimethyl-2(3H)-thiazolone hydrazone,
N-acetyl-4-methyl-3-phenyl-2(3H)-thiazolone hydrazone,
N-acetyl-4,5-dimethyl-3-phenyl-2(3H)-thiazolone hydrazone,
N-acetyl-3,4-diphenyl-2(3H)-thiazolone hydrazone,
N-acetyl-4-p-biphenylyl-3-phenyl-2(3H)-thiazolone hydrazone,
N-acetyl-4-(4-methoxy)phenyl-3-phenyl-2(3H)-thiazolone hydrazone,
N-acetyl-4-tert.butyl-3-phenyl-2(3H)-thiazolone hydrazone,
N-acetyl-3,4,5-triphenyl-2(3H)-thiazolone hydrazone,
N-acetyl-3-methyl-2(3H)-benzothiazolone hydrazone,
N-acetyl-3-ethyl-2(3H)-benzothiazolone hydrazone,
N-acetyl-3-butyl-2(3H)-benzothiazolone hydrazone,
N-acetyl-3-hexyl-2(3H)-benzothiazolone hydrazone,
N-acetyl-3-p-methylbenzyl-2(3H)-benzothiazolone hydrazone,
N-acetyl-3-methyl-2(3H)-oxazolone hydrazone,
N-acetyl-3-phenyl-2(3H)-oxazolone hydrazone,
N-acetyl-3-methyl-2(3H)-benzoxazolone hydrazone,
N-acetyl-3-phenyl-2(3H)-benzoxazolone hydrazone,
N-formyl-3-methyl-2(3H)-thiazolone hydrazone,
N-formyl-3,4-dimethyl-2(3H)-thiazolone hydrazone,
N-formyl-3-methyl-4-phenyl-2(3H)-thiazolone hydrazone,
N-formyl-4-(4-methoxy)phenyl-3-methyl-2(3H)-thiazolone hydrazone,
N-formyl-3-methyl-4-(4-nitrophenyl-2(3H)-thiazolone hydrazone,
N-formyl-4-[(1,1'-biphenyl)4-yl]-3-methyl-2(3H)-thiazolone hydrazone
N-formyl-3-methyl-4-(2-naphthalenyl)-2(3H)-thiazolone hydrazone
ethyl N-formyl-2-hydrazono-2,3-dihydro-3-methyl-4-thiazolecarboxylate
N-formyl-3,4,5-trimethyl-2(3H)-thiazolone hydrazone,
N-formyl-3,4,-dimethyl-5-phenyl-2(3H)-thiazolone hydrazone,
N-formyl-3,5,-dimethyl-4-phenyl-2(3H)-thiazolone hydrazone,
N-formyl-3-methyl-4,5-diphenyl-2(3H)-thiazolone hydrazone,
N-formyl-3-ethyl-4,5-dimethyl-2(3H)-thiazolone hydrazone,
N-formyl-4-methyl-3-phenyl-2(3H)-thiazolone hydrazone,
N-formyl-3,4-diphenyl-2(3H)-thiazolone hydrazone,
N-formyl-4-p-biphenylyl-3-phenyl-2(3H)-thiazolone hydrazone,
N-formyl-4-(4-methoxy)phenyl-3-phenyl-2(3H)-thiazolone hydrazone,
N-formyl-4-tert.butyl-3-phenyl-2(3H)-thiazolone hydrazone,
N-formyl-4,5-dimethyl-3-phenyl-2(3H)-thiazolone hydrazone,
N-formyl-5-methyl-3,4-diphenyl-2(3H)-thiazolone hydrazone,
N-formyl-3,4,5-triphenyl-2(3H)-thiazolone hydrazone,
N-formyl-3-methyl-2(3H)-benzothiazolone hydrazone,
N-formyl-3-ethyl-2(3H)-benzothiazolone hydrazone,
N-formyl-3-butyl-2(3H)-benzothiazolone hydrazone,
N-formyl-3-hexyl-2(3H)-benzothiazolone hydrazone,
N-formyl-3-p-methylbenzyl-2(3H)-benzothiazolone hydrazone,
N-formyl-3-methyl-2(3H)-oxazolone hydrazone,
N-formyl-3-phenyl-2(3H)-oxazolone hydrazone,
N-formyl-3-methyl-2(3H)-benzoxazolone hydrazone and
N-formyl-3-phenyl-2(3H)-benzoxazolone hydrazone.

Among the compounds of formula (I), the following thiazolone hydrazone derivatives are particularly preferred:
3-methyl-2(3H)-thiazolone hydrazone,
3,4-dimethyl-2(3H)-thiazolone hydrazone,
4-tert.butyl-3-methyl-2(3H)-thiazolone hydrazone,
3-methyl-4-phenyl-2(3H)-thiazolone hydrazone,
3-methyl-4-(4-tolyl)-2(3H)-thiazolone hydrazone,
4-(4-methoxy)phenyl-3-methyl-2(3H)-thiazolone hydrazone,
4-(4-ethoxy)phenyl-3-methyl-2(3H)-thiazolone hydrazone,
4-(4-bromophenyl)-3-methyl-2(3H)-thiazolone hydrazone,
4-(3-bromophenyl)-3-methyl-2(3H)-thiazolone hydrazone,
4-(4-chlorophenyl)-3-methyl-2(3H)-thiazolone hydrazone,
4-(3-chlorophenyl)-3-methyl-2(3H)-thiazolone hydrazone,
3-methyl-4-(4-nitrophenyl)-2(3H)-thiazolone hydrazone,
3-methyl-4-(3-nitrophenyl)-2(3H)-thiazolone hydrazone,
4-[(1,1'-biphenyl)-4-yl]-3-methyl-2(3H)-thiazolone hydrazone,
ethyl 2-hydrazono-2,3-dihydro-3-methyl-4-thiazolecarboxylate,
3,4,5-trimethyl-2(3H)-thiazolone hydrazone,
3,4-dimethyl-5-phenyl-2(3H)-thiazolone hydrazone,
3,5-dimethyl-4-phenyl-2(3H)-thiazolone hydrazone,
3-methyl-4,5-diphenyl-2(3H)-thiazolone hydrazone,
5-ethyl-3-methyl-4-phenyl-2(3H)-thiazolone hydrazone,
4-(4-bromophenyl)-3-methyl-5-phenyl-2(3H)-thiazolone hydrazone,
3-methyl-5-phenyl-4-(4-tolyl)-2(3H)-thiazolone hydrazone,
5-(4-chlorophenyl)-4-phenyl-3-methyl-2(3H)-thiazolone hydrazone,
5-(4-chlorophenyl)-4-(4-methoxyphenyl)-3-methyl-2(3H)-thiazolone hydrazone,
ethyl 2-hydrazono-2,3-dihydro-3,4-dimethyl-4-thiazolecarboxylate,
4-amino-2-hydrazono-2,3-dihydro-3-methyl-5-thiazolecarbonitrile,
3-ethyl-4,5-dimethyl-2(3H)-thiazolone hydrazone,
ethyl 2-hydrazono-2,3-dihydro-3-ethyl-4-methylthiazolecarboxylate, 5-methyl-3-(1-methylethyl)-4-phenyl-2(3H)-thiazolone hydrazone,
3-(1-methylethyl)-4,5-diphenyl-2(3H)-thiazolone hydrazone,
4,5-dimethyl-3-propyl-2(3H)-thiazolone hydrazone,
4,5-diphenyl-3-propyl-2(3H)-thiazolone hydrazone,
3-butyl-4,5-diphenyl-2(3H)-thiazolone hydrazone,
4,5-dimethyl-3-(2-methylpropyl)-2(3H)-thiazolone hydrazone,
3-(2-methylpropyl)-4,5-diphenyl-2(3H)-thiazolone hydrazone,
3-(2-propenyl)-2(3H)-thiazolone hydrazone,
4-methyl-3-(2-propenyl)-2(3H)-thiazolone hydrazone,
4-tert.butyl-3-(2-propenyl)-2(3H)-thiazolone hydrazone,
4-phenyl-3-(2-propenyl)-2(3H)-thiazolone hydrazone,
4,5-dimethyl-3-(2-propenyl)-2(3H)-thiazolone hydrazone,
3-hydroxyethyl-2(3H)-thiazolone hydrazone,
3-hydroxyethyl-4-methyl-2(3H)-thiazolone hydrazone,
3-hydroxyethyl-4,5-dimethyl-2(3H)-thiazolone hydrazone,
3-aminoethyl-2(3H)-thiazolone hydrazone,
3-aminoethyl-4-methyl-2(3H)-thiazolone hydrazone,
3-aminoethyl-4,5-dimethyl-2(3H)-thiazolone hydrazone,
3-phenyl-2(3H)-thiazolone hydrazone,
4-methyl-3-phenyl-2(3H)-thiazolone hydrazone,
3,4-diphenyl-2(3H)-thiazolone hydrazone,
4,5-dimethyl-3-phenyl-2(3H)-thiazolone hydrazone,
4-p-biphenylyl-3-phenyl-2(3H)-thiazolone hydrazone,
4-(4-methoxy)phenyl-3-phenyl-2(3H)-thiazolone hydrazone,
4-tert.butyl-3-phenyl-2(3H)-thiazolone hydrazone,
5-methyl-3,4-diphenyl-2(3H)-thiazolone hydrazone,
3,4,5-triphenyl-2(3H)-thiazolone hydrazone,
3-methyl-4,5,6,7-tetrahydro-2(3H)-benzothiazolone hydrazone,
3-methyl-2(3H)-benzothiazolone hydrazone,
3-ethyl-2(3H)-benzothiazolone hydrazone,
3-butyl-2(3H)-benzothiazolone hydrazone,
3-hexyl-2(3H)-benzothiazolone hydrazone,
3-hydroxyethyl-2(3H)-benzothiazolone hydrazone and
3-aminoethyl-2(3H)-benzothiazolone hydrazone.

Some of the compounds of formula (I) are commercially obtainable. They can, however, also be prepared by methods of synthesis known from the literature, for example by the procedure described in Research Disclosure October 1978, pages 42-44, No. 17434, or in analogy with the method described in DE 1 049 381 B.

Suitable as couplers are, in particular, the following compounds or salts thereof: N-(3-dimethylaminophenyl) urea, 2,6-diaminopyridine, 2-amino-4-[(2-hydroxyethyl)amino]-anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 1,3-diamino-4-(2,3-dihydroxypropoxy)benzene, 1,3-diamino-4-(3-hydroxypropoxy)-benzene, 1,3-diamino-4-(2-methoxyethoxy)benzene, 2,4-diamino-1,5-di (2-hydroxyethoxy)-benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)-propane, di(2,4-diaminophenoxy)methane, 1,3-diamino-2,4-dimethoxybenzene, 2,6-bis-(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-4-methoxy-2-methylphenol, 5-[(2-hydroxyethyl)amino]-2-methylphenol, 3-[(2-hydroxyethyl)amino]phenol, 3-[(2-methoxyethyl)amino]phenol, 5-amino-2-ethylphenol, 5-amino-2-methoxyphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 2,6-dihydroxy-3,4-dimethylpyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxy-ethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

Suitable persulfate salts are, for example, potassium persulfate, sodium persulfate or ammonium persulfate as well as mixtures thereof.

The ready-to-use colorant (A) contains the persulfate salts in a total amount from about 0.01 to 10 weight percent and preferably from about 0.1 to 5 weight percent.

Besides the compounds of formula (I) and the couplers, the colorant of the invention can optionally also contain other common, physiologically harmless direct dyes from the group of cationic and anionic dyes, disperse dyes, azo dyes, quinone dyes and triphenylmethane dyes.

The direct dyes are contained in the ready-to-use colorant (A) in an amount from about 0.01 to 10 weight percent and preferably from about 0.1 to 5 weight percent.

Besides the compounds of formula (I), the colorants of the invention can optionally contain other common developers, for example: 1,4-diaminobenzene (p-phenylenediamine), 1,4-diamino-2-methylbenzene (p-toluylenediamine), 1,4-diamino-2-(thiophen-2-yl)benzene, 1,4-diamino-2-(thiophen-3-yl)benzene, 4-(2,5-diaminophenyl)-2-[(diethylamino)methyl]thiophene, 2-chloro-3-(2,5-diaminophenyl)thiophene, 1,4-diamino-2-(pyridin-3-yl)benzene, 2,5-diaminobiphenyl, 2,5-diamino-4'-(1-methylethyl)-1,1'-biphenyl, 2,3',5-triamino-1,1'-biphenyl, 1,4-diamino-2-methoxymethylbenzene, 1,4-diamino-2-aminomethylbenzene, 1,4-diamino-2-[(phenylamino)methyl]benzene, 1,4-diamino-2-{[ethyl-(2-hydroxyethyl)amino]methyl}benzene, 1,4-diamino-2-hydroxymethylbenzene, 4-[di(2-hydroxyethyl)amino]aniline, 4-{[(4-aminophenyl)methyl]amino}aniline, 4-[(4-aminophenylamino)methyl]phenol, 1,4-diamino-N-(4-pyrrolidin-1-ylbenzyl)benzene, 1,4-diamino-N-furan-3-ylmethylbenzene, 1,4-diamino-N-thiophen-2-ylmethylbenzene, 1,4-diamino-N-furan-2-ylmethylbenzene, 1,4-diamino-N-thiophen-3-ylmethylbenzene, 1,4-diamino- N-benzylbenzene, 1,4-diamino-2-(1-hydroxyethyl)-benzene, 1,4-diamino-2-(2-hydroxyethyl)benzene, 1,3-bis-[(4-aminophenyl)(2-hydroxyethyl)amino]-2-propanol, 1,8-bis-(2,5-diaminophenoxy)-3,6-dioxaoctane, 2,5-diamino-4'-hydroxy-1,1'-biphenyl, 2,5-diamino-2'-trifluoromethyl-1,1'-biphenyl, 2,4',5-triamino-1,1'-biphenyl, 4-aminophenol, 4-amino-3-methylphenol, 4-methylaminophenol, 4-amino-2-(amino-methyl)phenol, 4-amino-2-[(2-hydroxyethyl)amino]methylphenol, 4-amino-2-(methoxymethyl)phenol, 5-aminosalicylic acid, 2,4,5,6-tetraaminopyrimidine, 2,5,6-triamino-4-(1H)-pyrimidone, 4,5-diamino-1-(2-hydroxyethyl)-1H-pyrazole, 4,5-diamino-1-pentyl-1H-pyrazole, 4,5-diamino-1-(phenylmethyl)-1H-pyrazole, 4,5-diamino-1-(4-methoxyphenyl)methyl-1H-pyrazole, 2-aminophenol, 2-amino-6-methylphenol, 2-amino-5-methylphenol, 1,2,4-trihydroxy-benzene, 2,4-diaminophenol, 1,4-dihydroxybenzene or 2-{[(4-aminophenyl)amino]methyl}-1,4-diaminobenzene.

The compounds of formula (I) and the couplers and additional developers are contained in the ready-o-use colorant (A) in a total amount from about 0.01 to 10 weight percent, and preferably from about 0.1 to 5 weight percent, each.

As a rule, the compounds of formula (I) and the couplers are stored separately from each other and only shortly before use are they mixed with each other and with the persulfate salt. If the compounds of formula (I), the couplers and the persulfate salt are solids, however, it is also possible to package them together and to prepare the ready-to-use colorant (A) shortly before use by mixing the compounds of formula (I), the couplers and the persulfate salt with water or with a liquid preparation containing the other ingredients of the agent.

As a rule, the colorant of the invention thus consists of several components that are mixed with each other before use. Preferably, the agent is in the form of a 2-component kit consisting of a dye carrier composition (A1) containing the compound of formula (I) and another dye carrier composition (A2) containing the couplers and the persulfate salts. Or the agent is in the form of a 3-component kit consisting of a dye carrier composition (A1) containing the compound of formula (I), another dye carrier composition (A2) containing the couplers, and a third component (A3) containing the persulfate salts.

Another object of the present invention is a multicomponent kit consisting of an agent of component (A1), an agent of component (A2), the persulfate possibly being packaged as component (A3) separately from component (A2), and optionally an agent for adjusting the pH (alkalinizing agent or acid). Naturally, the agents of component (A1) and (A2) can also consist of several individual components that are mixed together only just before use. Also possible is a 2-component kit the first component of which consists of the compounds of formula (I), the couplers and the persulfate salts and optionally other common powdered cosmetic additives (provided the afore-said contituents are solids) and the second component of which is water or a liquid cosmetic preparation optionally containing an agent for adjusting the pH. Particularly preferred, however, is a 2-component kit consisting of an agent of component (A1) and an agent of component (A2).

The aforesaid direct dyes can be contained in component (A2) in a total amount from about 0.02 to 20 weight percent and preferably from 0.2 to 10 weight percent, whereas the additional developers and the couplers can each be contained in a particular dye carrier composition [component (A1) or component (A2)] in a total amount from about 0.02 to 20 weight percent and preferably from about 0.2 to 10 weight percent.

The components (A1) and (A2) and the ready-to-use colorant (A) can be formulated, for example, as a solution, particularly an aqueous or aqueous-alcoholic solution, or as a cream, a gel or an emulsion. Their composition consists of a mixture of the compound of formula (I) or of the couplers and the additives commonly employed for such preparations.

The additives to the colorants commonly used in solutions, creams, emulsions, gels or aerosol foams are, for example, solvents such as water, lower aliphatic alcohols, for example ethanol, n-propanol and isopropanol or glycols such as glycerol and 1,2-propanediol, moreover wetting agents or emulsifiers from the classes of anionic, cationic, amphoteric or nonionic surface-active substances, such as the fatty alcohol sulfates, ethoxylated fatty alcohol sulfates, alkylsulfonates, alkylbenzenesulfonates, alkyltrimethyl-ammonium salts, alkylbetaines, ethoxylated fatty alcohols, ethoxylated nonylphenols, fatty alkanolamides, ethoxylated fatty esters, furthermore thickeners such as the higher fatty alcohols, starch or cellulose derivatives, perfumes, hair pretreatment agents, conditioners, hair swelling agents, preservatives, moreover vaselines, paraffin oil and fatty acids and also hair-care agents such as cationic resins, lanolin derivatives, cholesterol, pantothenic acid and betaine. The said constituents are employed in amounts commonly used for such purposes, for example the wetting agents and emulsifiers at a concentration from about 0.5 to 30 weight percent [always based on component (A1) or (A2)], the thickeners in an amount from about 0.1 to 25 wt. % [always based on component (A1) or (A2)] and the hair-care agents at a concen-tration from about 0.1 to 5.0 weight percent [always based on component (A1) or (A2)].

The pH of the ready-to-use colorant (A) and of the dye carrier compositions (A1) and (A2) is from about 3 to 12 and preferably from 3 to 10, the pH of the ready-to-use colorant (A) as a rule being established upon mixing the individual components [for example component (A1) with component (A2)]. The pH of the ready-to-use colorant (A) and of the dye carrier compositions (A1) and (A2) is preferably from about 3 to 7 when diaminobenzene derivatives are used as couplers, and from about 6 to 10 when derivatives of aminophenol or dihydroxybenzene are used as the couplers.

If necessary, however, to adjust the pH of components (A1) and (A2) and of the ready-to-use colorant (A) to the value desired for coloring, it is also possible to use alkalinizing agents, for example ammonia, alkali metal hydroxides, alkaline earth metal hydroxides, alkali metal acetates, alkaline earth metal acetates, alkali metal carbonates or alkaline earth metal carbonates, or else acids, for example lactic acid, acetic acid, tartaric acid, phosphoric acid, hydrochloric acid, citric acid, ascorbic acid or boric acid.

The ready-to-use colorant is prepared just before use by mixing components (A1) and (A2) or (A1), (A2) and (A3)—optionally by also adding an alkalinizing agent or an acid. The colorant is then applied to the fibers, particularly to human hair. Depending on the desired color depth, this mixture is then allowed to act for about 5 to 60 minutes and preferably from about 15 to 30 minutes at a temperature from about 20 to 50° C. and particularly from about 30 to 40° C. The fibers are then rinsed with water, optionally washed with a shampoo and then dried.

The colorant of the invention imparts to the fibers, particularly keratin fibers, for example to human hair, a uniform, particularly brilliant, intense and lasting coloration, with a wide range of yellow to blue shades being possible. The requirement for resistance to perspiration is met to an unusually high degree.

The following examples will explain the subject matter of the invention in greater detail without limiting its scope to these examples.

EXAMPLES

Example 1a

Synthesis of 3,4-dimethyl-2(3H)-thiazolone hydrazone hydrochloride

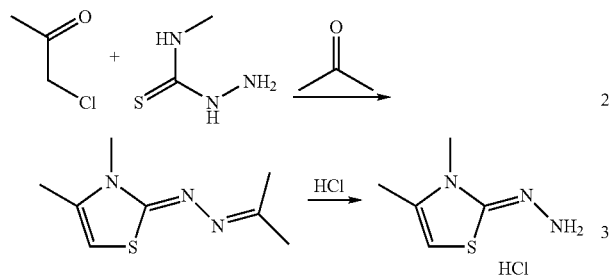

Step A: 3,4-Dimethyl-2(3H)-thiazolone-(1-methylethylidene)hydrazone 21 g (200 mmol) of 4-methyl-3-thiosemicarbazide in 1000 mL of acetone was heated at reflux for 2 hours. To the solution was then added dropwise 20.4 g (220 mmol) of chloroacetone. The reaction mixture was heated at reflux for 7 hours and then concentrated. The resulting crude product was recrystallized from acetone. This gave 23 g of an orange powder (63% of the theoretical).

Melting point 139-139.6° C. $^1$H-NMR (DMSO, 300 MHz): δ=6.72 [s, broad, 1H, H—C(5)]; δ=3.67 (s, 3H, N—CH3); δ=2.27 [d, J=0.9 Hz, 3H, CH3-C(4)]; δ=2.17 (s, 3H, CH3); δ=2.07 (s, 3H, CH3). $^{13}$C-NMR (DMSO, 300 MHz): 169.16; 164.14; 139.02 C(4); 103.36 C(5); 34.47 (CH$_3$N); 24.60; 19.91; 13.53 (CH$_3$—C(4). MS (ESI): 184 (M$^+$+1)

Step B: 3,4-Dimethyl-2(3H)-thiazolone hydrazone hydrochloride 3.5 g (19 mmol) of 3,4-dimethyl-2(3H)-thiazolone-(1-methylethylidene)hydrazone from step A in 60 mL of 6M hydrochloric acid was heated at 50° C. for 30 minutes. The reaction mixture was then concentrated, and the crude product was recrystallized from ethanol. This gave 2 g (60% of the theoretical) of a pink powder.

Melting point 156.4-156.6° C. $^1$H-NMR (DMSO, 300 MHz): δ=6.58 [q, J=0.9 Hz, 1H, H—C(5)]; δ=3.41 (s, 3H, N—CH3); δ=2.18 [d, J=0.9 Hz, 3H, CH3-C(4)]; MS (ESI): 144 (M$^+$+1) $^{13}$C-NMR (DMSO, 300 MHz): 172.30 C(2); 138.79 C(4); 101.43 C(5); 32.92 (CH$_3$N); 13.40 CH$_3$—(C4).

| CHN Analysis: [C$_5$H$_9$N$_3$S(0.96 HCl)(0.5 EtOH)]: | | | | | |
|---|---|---|---|---|---|
| | % C | % H | % N | % S | % Cl |
| Calculated: | 35.81 | 6.49 | 20.88 | 15.93 | 16.90 |
| Found: | 35.20 | 6.300 | 21.00 | 15.4 | 16.80 |

Examples 1b-1g

Synthesis of 2(3H) Thiazolone Hydrazones of Formula (I) (General Method of Synthesis)

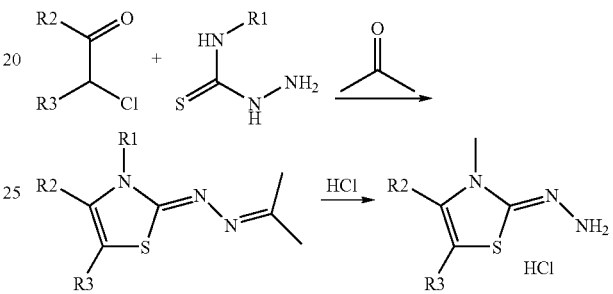

Step A: 4 mmol of substituted thiosemicarbazide in 20 mL of acetone was heated at reflux for 2 hours. To the solution was then added dropwise 4.4 mmol of α-chloroketone. The reaction mixture was heated at reflux for 7 hours and then concentrated. The resulting 2(3H)-thiazolone-1-(methylethylidene)hydrazone derivative was recrystallized from acetone.

Step B: 2 mmol of the 2(3H)-thiazolone-1-(methylethylidene)hydrazone derivative from step A in 10 mL of 6M hydrochloric acid was heated at 50° C. for 30 minutes. The reaction mixture was then concentrated, and the crude product was recrystallized from ethanol or butanol.

1b.) 3-Methyl-4-phenyl-2(3H)-thiazolone hydrazone hydrochloride

From 4-methyl-3-thiosemicarbazide and phenacyl chloride.
$^1$H-NMR (DMSO/D$_2$O, 300 MHz): δ=7.49-7.42 (m, 5H, phenyl); δ=6.84 [s, 1H, H—C(5)]; δ=3.31 (s, 3H, N—CH$_3$). ESI-MS: 205 [M]$^+$ (100)

1c.) 4-tert Butyl-3-methyl-2(3H)-thiazolone hydrazone hydrochloride

From 4-methyl-3-thiosemicarbazide and 1-chloro-3,3-dimethyl-2-butanone.
$^1$H-NMR (DMSO/D$_2$O, 300 MHz): δ=6.55 [s, 1H, H—C(5)]; δ=3.60 (s, 3H, N—CH$_3$); δ=1.31 [s, 9H, (CH$_3$)$_3$]. ESI-MS: 185 [M]$^+$ (100).

1d.) 4-Methyl-3-(2-propenyl)-2(3H)-thiazolone hydrazone hydrochloride

From 4-(2-propenyl)-3-thiosemicarbazide and chloroacetone.
$^1$H-NMR (DMSO/D$_2$O, 300 MHz): δ=6.58 [s, 1H, H—C (5)]; δ=5.94-5.81 (m, 1H, allyl); δ=5.22 (dd, 1H, J=0.9 Hz, J=10.5 Hz, allyl); δ=4.94 (dd, 1H, J=0.9 Hz, J=17.1 Hz, allyl); δ=4.57 (m, 2H, N—CH$_2$); δ=2.16 [s, 3H, CH$_3$—C(4)]. ESI-MS: 169 [M]$^+$ (100).

1e.) 4-Phenyl-3-(2-propenyl)-2(3H)-thiazolone hydrazone hydrochloride

From 4-(2-propenyl)-3-thiosemicarbazide and phenacyl chloride.

$^1$H-NMR (DMSO/D$_2$O, 300 MHz): δ=7.50-7.42 (m, 5H, phenyl); δ=6.81 [s, 1H, H—C(5)]; δ=5.77-5.63 (m, 1H, allyl); δ=5.15 (dd, 1H, J=0.9 Hz, J=10.5 Hz, allyl); δ=4.80 (dd, 1H, J=0.9 Hz, J=17.1 Hz, allyl); δ=4.40 (m, 2H, N—CH$_2$); δ=1.27 [s, 9H, CH$_3$—C(4)] ESI-MS: 231 [M]$^+$ (100).

1f.) 4-tert-Butyl 3-(2-propenyl)-2(3H)-thiazolone hydrazone hydrochloride

From 4-(2-propenyl)-3-thiosemicarbazide and 1-chloro-3,3-dimethyl-2-butanone.

$^1$H-NMR (DMSO/D$_2$O, 300 MHz): δ=6.55 [s, 1H, H—C-(5)]; δ=5.90-5.77 (m, 1H, allyl); δ=5.21 (d, 1H, J=9.0 Hz, allyl); δ=4.81-4.75 (m, 3H, allyl); δ=1.31 [s, 9H, (CH$_3$)$_3$] ESI-MS: 211 [M]$^+$ (100).

1g.) 3,4,5-Trimethyl-2(3H)thiazolone hydrazone hydrochloride

From 4-methyl-3-thiosemicarbazide and 3-chloro-2-butanone.

$^1$H-NMR (DMSO/D$_2$O, 300 MHz): δ=3.55 (s, 3H, N—CH$_3$); δ=2.16 (s, 3H, CH$_3$); δ=2.12 (s, 3H, CH$_3$). ESI-MS: 157 [M]$^+$ (100).

Examples 2-26

Colorants with 3-methyl-2(3H)-benzothiazolone hydrazone hydrochloride

| Component (A1) | |
|---|---|
| 4.00 g | of decylpolyglucose (Plantaren ® 2000), 50% aqueous solution |
| 0.20 g | of disodium ethylenediaminetetraacetate hydrate |
| 5.00 g | of ethanol |
| 0.58 g | of 3-methyl-2(3H)-benzothiazolone hydrazone hydrochloride hydrate |
| to 100.00 g | water, demineralized |
| Component (A2) | |
| Y g | of coupler as per Table 1 |
| 0.40 g | of potassium persulfate |

At room temperature (20-25° C.) or with slight heating (35-40° C.), the above components were uniformly mixed with one another. When necessary, the pH of the ready-to-use colorant (A) was adjusted to the value indicated in Table 1 with sodium hydroxide, sodium carbonate, ammonia or citric acid.

The ready-to-use hair colorant was applied to bleached hair and uniformly distributed with a brush. After an exposure time of 30 min at 40° C., the hair was rinsed with lukewarm water washed with a shampoo, rinsed with lukewarm water and then dried.

The amount of coupler used and the colorations obtained are summarized in the following Table 1.

TABLE 1

| Example No. | Coupler Used (Quantity in g) | pH | Shade |
|---|---|---|---|
| 2 | 1,3-diaminobenzene (0.27 g) | 7.0 | ruby-red |
| 3 | 2,4-diamino-1-(2-hydroxyethoxy)-benzene sulfate (0.66 g) | 7.5 | mahogany colors |
| 4 | 2-amino-4-[(2-hydroxyethyl)-amino]anisole sulfate (0.74 g) | 6.0 | mahogany colors |
| 5 | 1,3-di(2,4-diaminophenoxy)-propane tetrahydrochloride (1.08 g) | 6.2 | mahogany colors |
| 6 | 1,3-diamino-4-methoxybenzene (0.34 g) | 7.7 | mahogany colors |
| 7 | 1,3-diamino4-methylbenzene (3.0 g) | 6.1 | ruby red |
| 8 | N-(3-dimethylaminophenyl)urea (0.44 g) | 6.6 | violet |
| 9 | 3-aminophenol (0.27 g) | 3.6 | ruby red |
| 10 | 5-amino-2-methylphenol (0.31 g) | 3.9 | copper colors |
| 11 | 3-dimethylaminophenol (0.34 g) | 3.6 | raspberry red |
| 12 | 1,3-dihydroxybenzene (0.27 g) | 3.8 | copper colors |
| 13 | 1-naphthol (0.36 g) | 3.7 | orange |
| 14 | 1,5-dihydroxynaphthalene (0.40 g) | 3.2 | copper colors |
| 15 | 1,7-dihydroxynaphthalene (0.40 g) | 3.7 | pink-red |
| 16 | 8-hydroxyquinoline (0.36 g) | 3.4 | copper colors |
| 17 | 2,3-diaminopyridine (0.27 g) | 9.6 | cherry-red |
| 18 | 2-amino-3-hydroxypyridine (0.27 g) | 9.1 | red-violet |
| 19 | 4-amino-1H-indole (0.33 g) | 7.5 | violet |
| 20 | 1,2-diaminobenzene (0.27 g) | 6.1 | brown |
| 21 | 2-aminophenol (0.27 g) | 3.6 | brown-mahogany |
| 22 | 1,3-diaminobenzene (0.14 g) 3-aminophenol (0.14 g) | 6.5 | ruby red |
| 23 | 1,3-diaminobenzene (0.14 g) 1,3-dihydroxybenzene (0.14 g) | 6.2 | ruby red |
| 24 | 1,3-diaminobenzene (0.14 g) N-(3-dimethylaminophenyl)urea (0.22 g) | 7.7 | mahogany colors |
| 25 | N-(3-dimethylaminophenyl)urea (0.22 g) 1,3-dihydroxybenzene (0.14 g) | 6.4 | violet |
| 26 | 1,3-diaminobenzene (0.05 g) 2,4-diamino-1-(2-hydroxyethoxy)-benzene sulfate (0.12 g) 5-amino-2-methylphenol (0.06 g) 3-aminophenol (0.05 g) 1,3-dihydroxybenzene (0.05 g) | 9.6 | mahogany colors |

Examples 27-35

Colorants with 3,4-dimethyl-2(3H)-thiazolone hydrazone hydrochloride

| Component (A1) | |
|---|---|
| 4.00 g | of decylpolyglucose (Plantaren ® 2000), 50% aqueous solution |
| 0.20 g | of disodium ethylenediaminetetraacetate hydrate |
| 5.00 g | of ethanol |
| 0.45 g | of 3,4-dimethyl-2(3H)-thiazolone hydrazone hydrochloride |
| to 100.00 g | water, demineralized |
| Component (A2) | |
| Y g | of coupler as per Table 2 |
| 0.40 g | of potassium persulfate |

At room temperature (20-25° C.) or with slight heating (35-40° C.), the above components were uniformly mixed with one another. When necessary, the pH of the ready-touse colorant (A) was adjusted to the value indicated in Table 2 with sodium hydroxide, sodium carbonate, ammonia or citric acid.

The ready-to-use hair colorant was applied to bleached hair and uniformly distributed with a brush. After an exposure time of 30 min at 40° C., the hair was rinsed with lukewarm water washed with a shampoo, rinsed with lukewarm water and then dried.

The amount of coupler used and the colorations obtained are summarized in the following Table 2.

TABLE 2

| Example No. | Coupler Used (Quantity in g) | pH | Shade |
|---|---|---|---|
| 27 | 1,3-diaminobenzene (0.27 g) | 7.2 | Bordeaux red |
| 28 | 2,4-diamino-1-(2-hydroxyethoxy)-benzene sulfate (0.67 g) | 6.7 | dark Bordeaux red |
| 29 | N-(3-dimethylaminophenyl)urea (0.44 g) | 7.3 | blue |
| 30 | 3-aminophenol (0.27 g) | 7.2 | raspberry red |
| 31 | 5-amino-2-methylphenol (0.31 g) | 6.6 | ruby red |
| 32 | 5-[(2-hydroxyethyl)amino]-2-methyl-phenol sulfate (2:1) (0.54 g) | 6.8 | orange |
| 33 | 1,3-dihydroxybenzene (0.27 g) | 9.9 | pink-copper |
| 34 | 1-naphthol (0.36 g) | 9.7 | pink |
| 35 | 1,3-diaminobenzene (0.05 g) 2,4-diamino-1-(2-hydroxyethoxy)-benzene sulfate (0.12 g) 5-amino-2-methylphenol (0.06 g) 3-aminophenol (0.05 g)\ 1,3-dihydroxybenzene (0.05 g) | 9.8 | dark violet-eggplant |

Examples 36-65

Colorants with 2(3H)-thiazolone hydrazone of formula (I) (Examples 1b-1g)

Component (A1)

| | | |
|---|---|---|
| 4.00 g | of decylpolyglucose (Plantaren ® 2000), 50% aqueous solution | |
| 0.20 g | of disodium ethylenediaminetetraacetate hydrate | |
| 5.00 g | of ethanol | |
| X g | of 2(3H)-thiazolone hydrazone of formula (I) (1b–1g) | |
| to 100.00 g | water, demineralized | |

Component (A2)

| | |
|---|---|
| Y g | of coupler as per Table 3 |
| 0.80 g | of potassium persulfate |

At room temperature (20-25° C.) or with slight heating (35-40° C.), the above components were uniformly mixed with one another. When necessary, the pH of the ready-to-use colorant (A) was adjusted to the value indicated in Table 3 with sodium hydroxide, sodium carbonate, ammonia or citric acid.

The ready-to-use hair colorant was applied to bleached buffalo hair and uniformly distributed with a brush. After an exposure time of 30 min at 40° C., the hair was rinsed with lukewarm water washed with a shampoo, rinsed with lukewarm water and then dried.

The amount of 2(3H)-thiazolone hydrazone of formula (I) (1b-1g) and of coupler used and the colorations obtained are summarized in the following Table 3.

TABLE 3

| Example No. | Derivative of Formula (I) as Per Example No. (Amount in g) | Coupler Used (Amount in g) | pH | Shade |
|---|---|---|---|---|
| 36 | Example 1b (0.60 g) | 1,3-diaminobenzene (0.27 g) | 9.6 | Bordeaux red |
| 37 | Example 1c (0.55 g) | 1,3-diaminobenzene (0.27 g) | 9.6 | Bordeaux red |
| 38 | Example 1d (0.51 g) | 1,3-diaminobenzene (0.27 g) | 9.6 | Bordeaux red |
| 39 | Example 1e (0.67 g) | 1,3-diaminobenzene (0.27 g) | 9.6 | Bordeaux red |
| 40 | Example 1f (0.62 g) | 1,3-diaminobenzene (0.27 g) | 9.6 | Bordeaux red |
| 41 | Example 1g (0.48 g) | 1,3-diaminobenzene (0.27 g) | 9.2 | violet-eggplant |
| 42 | Example 1b (0.60 g) | 2,4-diamino-1-(2-hydroxyethoxy)benzene sulfate (0.67 g) | 9.6 | Bordeaux red |
| 43 | Example 1c (0.55 g) | 2,4-diamino-1-(2-hydroxyethoxy)benzene sulfate (0.67 g) | 9.6 | Bordeaux red |
| 44 | Example 1d (0.51 g) | 2,4-diamino-1-(2-hydroxyethoxy)benzene sulfate (0.67 g) | 9.6 | Bordeaux red |
| 45 | Example 1e (0.67 g) | 2,4-diamino-1-(2-hydroxyethoxy)benzene sulfate (0.67 g) | 9.6 | Bordeaux red |
| 46 | Example 1f (0.62 g) | 2,4-diamino-1-(2-hydroxyethoxy)benzene sulfate (0.67 g) | 9.6 | Bordeaux red |
| 47 | Example 1g (0.48 g) | 2,4-diamino-1-(2-hydroxyethoxy)benzene sulfate (0.67 g) | 9.4 | violet-eggplant |
| 48 | Example 1b (0.60 g) | N-(3-dimethylaminophenyl)urea (0.44 g) | 9.5 | blue |
| 49 | Example 1c (0.55 g) | N-(3-dimethylaminophenyl)urea (0.44 g) | 9.5 | blue |
| 50 | Example 1d (0.51 g) | N-(3-dimethylaminophenyl)urea (0.44 g) | 9.5 | blue |
| 51 | Example 1e (0.67 g) | N-(3-dimethylaminophenyl)urea (0.44 g) | 9.5 | blue |
| 52 | Example 1f (0.62 g) | N-(3-dimethylaminophenyl)urea (0.44 g) | 9.5 | blue |
| 53 | Example 1g (0.48 g) | N-(3-dimethylaminophenyl)urea (0.44 g) | 9.4 | blue |
| 54 | Example 1b (0.60 g) | 3-aminophenol (0.27 g) | 9.6 | raspberry red |
| 55 | Example 1c (0.55 g) | 3-aminophenol (0.27 g) | 9.6 | raspberry red |
| 56 | Example 1d (0.51 g) | 3-aminophenol (0.27 g) | 9.6 | raspberry red |
| 57 | Example 1e (0.67 g) | 3-aminophenol (0.27 g) | 9.6 | raspberry red |
| 58 | Example 1f (0.62 g) | 3-aminophenol (0.27 g) | 9.6 | raspberry red |
| 59 | Example 1g (0.48 g) | 3-aminophenol (0.27 g) | 9.3 | violet-red |
| 60 | Example 1b (0.60 g) | 1,3-dihydroxybenzene (0.27 g) | 9.6 | red-orange |
| 61 | Example 1c (0.55 g) | 1,3-dihydroxybenzene (0.27 g) | 9.6 | red-orange |
| 62 | Example 1d (0.51 g) | 1,3-dihydroxybenzene (0.27 g) | 9.6 | red-orange |
| 63 | Example 1e (0.67 g) | 1,3-dihydroxybenzene (0.27 g) | 9.6 | red-orange |
| 64 | Example 1f (0.62 g) | 1,3-dihydroxybenzene (0.27 g) | 9.6 | red-orange |
| 65 | Example 1g (0.48 g) | 1,3-dihydroxybenzene (0.27 g) | 9.6 | raspberry red |

Unless otherwise indicated, all percentages in the present patent application are by weight.

The invention claimed is:

1. An agent for coloring fibers (A), containing:
   (a) at least one hydrazone derivative of formula (I) or a physiologically compatible salt thereof,

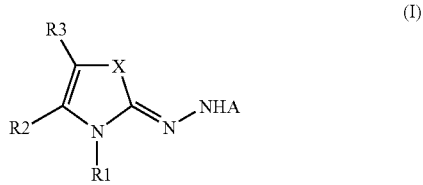

wherein

X denotes oxygen or sulfur,

A denotes hydrogen, an acetyl group, a trifluoroacetyl group, a formyl group, a $(C_1-C_6)$-alkylsulfonyl group or an arylsulfonyl group;

R1 denotes a saturated or unsaturated $(C_1-C_{12})$-alkyl group, a halogen (F, Cl, Br, I)-substituted $(C_1-C_{12})$-alkyl group, a hydroxy-$(C_1-C_{12})$-alkyl group, an amino-$(C_1-C_{12})$-alkyl group, a sulfonic acid-$(C_1-C_{12})$-alkyl group, a formyl group, a C(O)—$(C_1-C_{12})$-alkyl group, a C(O)-phenyl group, a C(O)NH—$(C_1-C_{12})$ alkyl group, a C(O)NH-phenyl group, a substituted or unsubstituted phenyl group or a benzyl group;

R2 and R3 can be equal or different and independently of each other denote hydrogen, a halogen atom (F, Cl, Br, I), a saturated or unsaturated $(C_1-C_{12})$-alkyl group, a halogen (F, Cl, Br, I)-substituted $(C_1-C_{12})$-alkyl group, a hydroxyl-$(C_1-C_{12})$-alkyl group, a $(C_1-C_{12})$-alkoxy group, a cyano group, a nitro group, an amino group, a $(C_1-C_{12})$-alkylamino group, a $(C_1-C_{12})$-dialkylamino group, a carboxylic acid group, a C(O)O($C_1-C_{12}$)-alkyl group, a substituted or unsubstituted C(O)O-phenyl group, a substituted or unsubstituted phenyl group or a naphthyl group;

or R2 and R3 together with the remainder of the molecule form a heterocyclic or carbocyclic, saturated or unsaturated, substituted or unsubstituted ring system;

(b) at least one known coupler or a physiologically compatible salt thereof; and (c) a persulfate salt as oxidant.

2. The agent according to claim 1, wherein X denotes sulfur and A stands for hydrogen, R1 denotes a saturated or unsaturated $(C_1-C_{12})$-alkyl group, a hydroxy-$(C_1-C_{12})$-alkyl group, an amino-$(C_1-C_{12})$-alkyl group, or a substituted or unsubstituted phenyl group, and R2 and R3 independently of each other denote hydrogen, a saturated or unsaturated $(C_1-C_{12})$-alkyl group, a cyano group, a nitro group, an amino group, a $(C_1-C_{12})$-alkylamino group, a $(C_1-C_{12})$-dialkylamino group, a C(O)O-alkyl group or a substituted or unsubstituted phenyl group or a naphthyl group, or R2 and R3 together with the remainder of the molecule form a carbocyclic, unsaturated, substituted or unsubstituted ring system.

3. The agent according to claim 1, wherein the at least one hydrazone derivative of formula (I) is selected from the group consisting of 3-methyl-2(3H)-thiazolone hydrazone,
3,4-dimethyl-2(3H)-thiazolone hydrazone,
4-tert.butyl-3-methyl-2(3H)-thiazolone hydrazone,
3-methyl-4-phenyl-2(3H)-thiazolone hydrazone,
3-methyl-4-(4-tolyl)-2(3H)-thiazolone hydrazone,
4-(4-methoxy)phenyl-3-methyl-2(3H)-thiazolone hydrazone,
4-(4-ethoxy)phenyl-3-methyl-2(3H)-thiazolone hydrazone,
4-(4-bromophenyl)-3-methyl-2(3H)-thiazolone hydrazone,
4-(3-bromophenyl)-3-methyl-2(3H)-thiazolone hydrazone,
4-(4-chlorophenyl)-3-methyl-2(3H)-thiazolone hydrazone,
4-(3-chlorophenyl)-3-methyl-2(3H)-thiazolone hydrazone,
3-methyl-4-(4-nitrophenyl)-2(3H)-thiazolone hydrazone,
3-methyl-4-(3-nitrophenyl)-2(3H)-thiazolone hydrazone,
4-[(1,1'-biphenyl)-4-yl]-3-methyl-2(3H)-thiazolone hydrazone,
3-methyl-4-(2-naphthalenyl)-2(3H)-thiazolone,
ethyl 2-hydrazono-2,3-dihydro-3-methyl-4-thiazolecarboxylate,
3,4,5-trimethyl-2(3H)-thiazolone hydrazone,
3,4-dimethyl-5-phenyl-2(3H)-thiazolone hydrazone,
3,5-dimethyl-4-phenyl-2(3H)-thiazolone hydrazone,
3-methyl-4,5-diphenyl-2(3H)-thiazolone hydrazone,
5-ethyl-3-methyl-4-phenyl-2(3H)-thiazolone hydrazone,
4-(4-bromophenyl)-3-methyl-5-phenyl-2(3H)-thiazolone hydrazone,
3-methyl-5-phenyl-4-(4-tolyl)-2(3H)-thiazolone hydrazone,
5-(4-chlorophenyl)-4-phenyl-3-methyl-2(3H)-thiazolone hydrazone,
5-(4-chlorophenyl)-4-(4-methoxyphenyl)-3-methyl-2(3H)-thiazolone hydrazone,
ethyl 2-hydrazono-2,3-dihydro-3,4-dimethyl-4-thiazolecarboxylate,
4-amino-2-hydrazono-2,3-dihydro-3-methyl-5-thiazolecarbonitrile,
3-ethyl-4,5-dimethyl-2(3H)-thiazolone hydrazone,
ethyl 2-hydrazono-2,3-dihydro-3-ethyl-4-methylthiazolecarboxylate,
5-methyl-3-(1-methylethyl)-4-phenyl-2(3H)-thiazolone hydrazone,
4,5-dimethyl-3-(1-methylethyl)-2(3H)-thiazolone hydrazone,
3-(1-methylethyl)-4,5-diphenyl-2(3H)-thiazolone hydrazone,
4,5-dimethyl-3-propyl-2(3H)-thiazolone hydrazone,
4,5-diphenyl-3-propyl-2(3H)-thiazolone hydrazone,
3-butyl-4,5-diphenyl-2(3H)-thiazolone hydrazone,
4,5-dimethyl-3-(2-methylpropyl)-2(3H)-thiazolone hydrazone,
3-(2-methylpropyl)-4,5-diphenyl-2(3H)-thiazolone hydrazone,
3-hydroxyethyl-2(3H)-thiazolone hydrazone,
3-hydroxyethyl-4-methyl-2(3H)-thiazolone hydrazone,
3-hydroxyethyl-4,5-dimethyl-2(3H)-thiazolone hydrazone,
3-aminoethyl-2(3H)-thiazolone hydrazone,
3-aminoethyl-4-methyl-2(3H)-thiazolone hydrazone,
3-aminoethyl-4,5-dimethyl-2(3H)-thiazolone hydrazone,
3,4-diphenyl-2(3H)-thiazolone hydrazone,
4-methyl-3-phenyl-2(3H)-thiazolone hydrazone,
4-p-biphenylyl-3-phenyl-2(3H)-thiazolone hydrazone,
4-(4-methoxy)phenyl-3-phenyl-2(3H)-thiazolone hydrazone,
4-tert.butyl-3-phenyl-2(3H)-thiazolone hydrazone,
4,5-dimethyl-3-phenyl-2(3H)-thiazolone hydrazone,
5-methyl-3,4-diphenyl-2(3H)-thiazolone hydrazone, 3,4,5-triphenyl-2(3H)-thiazolone hydrazone,
4,5-dimethyl-3-(phenylmethyl)-2(3H)-thiazolone hydrazone,
3-(2-propenyl)-2(3H)-thiazolone hydrazone,
4-methyl-3-(2-propenyl)-2(3H)-thiazolone hydrazone,
4-tert.butyl-3-(2-propenyl)-2(3H)-thiazolone hydrazone,
4-phenyl-3-(2-propenyl)-2(3H)-thiazolone hydrazone,
4,5-dimethyl-3-(2-propenyl)-2(3H)-thiazolone hydrazone,
4,5-diphenyl-3-(2-propenyl)-2(3H)-thiazolone hydrazone,
ethyl 2-hydrazono-2,3-dihydro-3-[(phenylamino)carbonyl]-4-methylthiazolecarboxylate,
3-methyl-4,5,6,7-tetrahydro-2(3H)-benzothiazolone hydrazone,
3-methyl-2(3H)-benzothiazolone hydrazone,
3,6-dimethyl-2(3H)-benzothiazolone hydrazone,
6-chloro-3-methyl-2(3H)-benzothiazolone hydrazone,
7-chloro-3-methyl-2(3H)-benzothiazolone hydrazone,
6-hydroxy-3-methyl-2(3H)-benzothiazolone hydrazone,
5-methoxy-3-methyl-2(3H)-benzothiazolone hydrazone,
7-methoxy-3-methyl-2(3H)-benzothiazolone hydrazone,
5,6-dimethoxy-3-methyl-2(3H)-benzothiazolone hydrazone,
5-ethoxy-3-methyl-2(3H)-benzothiazolone hydrazone,
6-ethoxy-3-methyl-2(3H)-benzothiazolone hydrazone,
3-methyl-5-nitro-2(3H)-benzothiazolone hydrazone,
3-methyl-6-nitro-2(3H)-benzothiazolone hydrazone,
5-acetamido-3-methyl-2(3H)-benzothiazolone hydrazone,
6-acetamido-3-methyl-2(3H)-benzothiazolone hydrazone,
5-anilino-3-methyl-2(3H)-benzothiazolone hydrazone,
6-anilino-3-methyl-2(3H)-benzothiazolone hydrazone,
2-hydrazono-2,3-dihydro-3-methyl-6-benzothiazolecarboxylic acid,
2-hydrazono-2,3-dihydro-3-methyl-4-benzothiazolesulfonic acid,
2-hydrazono-2,3-dihydro-3-methyl-5-benzothiazolesulfonic acid,
2-hydrazono-2,3-dihydro-3-methyl-6-benzothiazolesulfonic acid,
2-hydrazono-2,3-dihydro-3-methyl-7-benzothiazolesulfonic acid,
2-hydrazono-2,3-dihydro-N,N,3-trimethyl-6-benzothiazolesulfonamide,
[(2-hydrazono-2,3-dihydro-3-methyl-6-benzothiazolyl)oxy]acethydrazide,
3-methylnaphtho[2,3-d]thiazole-2(3H)-one hydrazone,
3-ethyl-2(3H)-benzothiazolone hydrazone,
6-ethoxy-3-ethyl-2(3H)-benzothiazolone hydrazone,
3-propyl-2(3H)-benzothiazolone hydrazone,
3-butyl-2(3H)-benzothiazolone hydrazone,
3-hexyl-2(3H)-benzothiazolone hydrazone,
3-hydroxyethyl-2(3H)-benzothiazolone hydrazone,
3-aminoethyl-2(3H)-benzothiazolone hydrazone,
3-p-methylbenzyl-2(3H)-benzothiazolone hydrazone,
2-hydrazono-2,3-dihydro-3-(2-hydroxyethyl)-6-benzothiazolecarboxylic acid,
2-hydrazono-2,3-dihydro-6-methoxy-3(2H)-benzothiazolepropanesulfonic acid
6-hexadecyloxy-2-hydrazono-3(2H)-benzothiazolepropanesulfonic acid,
ethyl 2-keto-3-benzothiazoline acetate hydrazone,
3-acetyl-2(3H)-benzothiazolone hydrazone,
2-hydrazono-3(2H)-benzothiazole carboxaldehyde,
3-methyl-2(3H)-oxazolone hydrazone,
3-phenyl-2(3H)-oxazolone hydrazone,
3-methyl-2(3H)-benzoxazolone hydrazone,
3-phenyl-2(3H)-benzoxazolone hydrazone,
N-acetyl-3-methyl-2(3H)-thiazolone hydrazone,
N-acetyl-3,4-dimethyl-2(3H)-thiazolone hydrazone,
N-acetyl-3-methyl-4-phenyl-2(3H)-thiazolone hydrazone,
N-acetyl-4-(4-methoxy)phenyl-3-methyl-2(3H)-thiazolone hydrazone,
N-acetyl-3-methyl-4-(4-nitro)phenyl-2(3H)-thiazolone hydrazone,
N-acetyl-4-[(1,1'-biphenyl)4-yl]-3-methyl-2(3H)-thiazolone hydrazone,
N-acetyl-3-methyl-4-(2-naphthalenyl)-2(3H)-thiazolone hydrazone,
ethyl N-acetyl-2-hydrazono-2,3-dihydro-3-methyl-4-thiazolecarboxylate,
N-acetyl-3,4,5-trimethyl-2(3H)-thiazolone hydrazone,
N-acetyl-3,4,-dimethyl-5-phenyl-2(3H)-thiazolone hydrazone,
N-acetyl-3,5,-dimethyl-4-phenyl-2(3H)-thiazolone hydrazone,
N-acetyl-3-methyl-4,6-diphenyl-2(3H)-thiazolone hydrazone,
N-acetyl-3-ethyl-4,5-dimethyl-2(3H)-thiazolone hydrazone,
N-acetyl-4-methyl-3-phenyl-2(3H)-thiazolone hydrazone,
N-acetyl-3,4-diphenyl-2(3H)-thiazolone hydrazone,
N-acetyl-4-p-biphenylyl-3-phenyl-2(3H)-thiazolone hydrazone,
N-acetyl-4-(4-methoxy)phenyl-3-phenyl-2(3H)-thiazolone hydrazone,
N-acetyl-4-tert.butyl-3-phenyl-2(3H)-thiazolone hydrazone,
N-acetyl-4,5-dimethyl-3-phenyl-2(3H)-thiazolone hydrazone,
N-acetyl-5-methyl-3,4-diphenyl-2(3H)-thiazolone hydrazone,
N-acetyl-3,4,5-triphenyl-2(3H)-thiazolone hydrazone,
N-acetyl-3-methyl-2(3H)-benzothiazolone hydrazone,
N-acetyl-3-ethyl-2(3H)-benzothiazolone hydrazone,
N-acetyl-3-butyl-2(3H)-benzothiazolone hydrazone,
N-acetyl-3-hexyl-2(3H)-benzothiazolone hydrazone,
N-acetyl-3-p-methylbenzyl-2(3H)-benzothiazolone hydrazone,
N-acetyl-3-methyl-2(3H)-oxazolone hydrazone,
N-acetyl-3-phenyl-2(3H)-oxazolone hydrazone,
N-acetyl-3-methyl-2(3H)-benzoxazolone hydrazone,
N-acetyl-3-phenyl-2(3H)-benzoxazolone hydrazone,
N-formyl-3-methyl-2(3H)-thiazolone hydrazone,
N-formyl-3,4-dimethyl-2(3H)-thiazolone hydrazone,
N-formyl-3-methyl-4-phenyl-2(3H)-thiazolone hydrazone,
N-formyl-4-(4-methoxy)phenyl-3-methyl-2(3H)-thiazolone hydrazone,
N-formyl-3-methyl-4-(4-nitro)phenyl-2(3H)-thiazolone hydrazone,
N-formyl-4-[(1,1'-biphenyl)4-yl]-3-methyl-2(3H)-thiazolone hydrazone,
N-formyl-3-methyl-4-(2-naphthalenyl)-2(3H)-thiazolone hydrazone,
ethyl N-formyl-2-hydrazono-2,3-dihydro-3-methyl-4-thiazolecarboxylate,
N-formyl-3,4,5-trimethyl-2(3H)-thiazolone hydrazone,
N-formyl-3,4,-dimethyl-5-phenyl-2(3H)-thiazolone hydrazone, N-formyl-3,5,-dimethyl-4-phenyl-2(3H)-thiazolone hydrazone,
N-formyl-3-methyl-4,5-diphenyl-2(3H)-thiazolone hydrazone,
N-formyl-3-ethyl-4,5-dimethyl-2(3H)-thiazolone hydrazone,
N-formyl-4-methyl-3-phenyl-2(3H)-thiazolone hydrazone,
N-formyl-3,4-diphenyl-2(3H)-thiazolone hydrazone,
N-formyl-4-p-biphenylyl-3-phenyl-2(3H)-thiazolone hydrazone,
N-formyl-4-(4-methoxy)phenyl-3-phenyl-2(3H)-thiazolone hydrazone,
N-formyl-4-tert.butyl-3-phenyl-2(3H)-thiazolone hydrazone,
N-formyl-4,5-dimethyl-3-phenyl-2(3H)-thiazolone hydrazone,
N-formyl-5-methyl-3,4-diphenyl-2(3H)-thiazolone hydrazone,
N-formyl-3,4,5-triphenyl-2(3H)-thiazolone hydrazone,
N-formyl-3-methyl-2(3H)-benzothiazolone hydrazone,
N-formyl-3-ethyl-2(3H)-benzothiazolone hydrazone,
N-formyl-3-butyl-2(3H)-benzothiazolone hydrazone,
N-formyl-3-hexyl-2(3H)-benzothiazolone hydrazone,
N-formyl-3-p-methylbenzyl-2(3H)-benzothiazolone hydrazone,
N-formyl-3-methyl-2(3H)-oxazolone hydrazone,
N-formyl-3-phenyl-2(3H)-oxazolone hydrazone,
N-formyl-3-methyl-2(3H)-benzoxazolone hydrazone and
N-formyl-3-phenyl-2(3H)-benzoxazolone hydrazone.

4. The agent according to claim 1, wherein the at least one coupler is selected from the group consisting of
N-(3-dimethylaminophenyl)urea; 2,6-diaminopyridine; 2-amino-4-[(2-hydroxyethyl)amino]-anisole; 2,4-diamino-1-fluoro-5-methylbenzene; 2,4-diamino-1-methoxy-5-methylbenzene; 2,4-diamino-1-ethoxy-5-methylbenzene; 2,4-diamino-1-(2-hydroxyethoxy)-5-methyl benzene; 2,4-di[(2-hydroxyethyl)amino]-1,5-dimethoxybenzene; 2,3-diamino-6-methoxypyridine; 3-amino-6-methoxy-2-(methylamino)pyridine; 2,6-diamino-3,5-dimethoxypyridine; 3,5-diamino-2,6-dimethoxypyridine; 1,3-diaminobenzene; 2,4-diamino-1-(2-hydroxyethoxy)benzene; 1,3-diamino-4-(2,3-dihydroxyropoxy)benzene; 1,3-diamino-4-(3-hydroxypropoxy)-benzene; 1,3-diamino-4-(2-methoxyethoxy)benzene; 2,4-diamino-1,5-di(2-hydroxyethoxy)-benzene; 1-(2-aminoethoxy)-2,4-diaminobenzene; 2-amino-1-(2-hydroxyethoxy)-4-methylaminobenzene; 2,4-diaminophenoxyacetic acid; 3-[di(2-hydroxyethyl)amino]anhline; 4-amino-2-di[(2-hydroxyethyl)amino]-1-ethoxybenzene; 5-methyl-2-(1-methylethyl)phenol; 3-[(2-hydroxyethyl)amino]aniline; 3-[(2-aminoethyl)amino]aniline; 1,3-di(2,4-diaminophenoxy)-propane; di(2,4-diaminophenoxy)methane; 1,3-diamino-2,4-dimethoxybenzene; 2,6-bis-(2-hydroxyethyl)aminotoluene; 4-hydroxyindole; 3-dimethylaminophenol; 3-diethylaminophenol; 5-amino-2-methylphenol; 5-amino-4-fluoro-2-methylphenol; 5-amino-4-methoxy-2-methylphenol; 5-amino-4-ethoxy-2-methylphenol; 3-amino-2,4-dichlorophenol; 5-amino-2,4-dichlorophenol; 3-amino-2-methylphenol; 3-amino-2-chloro-6-methylphenol; 3-aminophenol; 2-[(3-hydroxyphenyl)amino]acetamide; 5-[(2-hydroxyethyl)amino]-4-methoxy-2-methylphenol; 5-[(2-hydroxyethyl)amino]-2-methylphenol; 3-[(2-hydroxyethylamino]phenol; 3-[(2-methoxyethyl)amino]phenol; 5-amino-2-ethylphenol; 5-amino-2-methoxyphenol; 2-(4-amino-2-hydroxyphenoxy)ethanol; 5-[(3-hydroxypropyl)amino]-2-methylphenol; 3-[(2,3-dihydroxypropyl)amino]-2-methylphenol; 3-[(2-hydroxyethyl)amino]-2-methylphenol; 2-amino-3-hydroxypyridine; 2,6-dihydroxy-3,4-dimethylpyridine; 5-amino-4-chloro-2-methylphenol; 1-naphthol; 2-methyl-1-naphthol; 1,5-dihydroxynaphthalene; 1,7-dihydroxynaphthalene; 2,3-dihydroxynaphthalene; 2,7-dihydroxynaphthalene; 2-methyl-1-naphthol acetate; 1,3-dihydroxybenzene; 1-chloro-2,4-dihydroxybenzene; 2-chloro-1,3-dihydroxybenzene; 1,2-dichloro-3,5-dihydroxy-4-methylbenzene; 1,5-dichloro-2,4-dihydroxybenzene; 1,3-dihydroxy-2-methylbenzene; 3,4-methylenedioxyphenol; 3,4-methylenedioxyaniline; 5-[(2-hydroxyethyl)amino]-1,3-benzodioxole; 6-bromo-1-hydroxy-3,4-methylenedioxybenzene; 3,4-diaminobenzoic acid; 3,4-dihydro-6-hydroxy-1,4(2H)-benzoxazine; 6-amino-3,4-dihydro-1,4(2H)benzoxazine; 3-methyl-1-phenyl-5-pyrazolone; 5,6-dihydroxyindole; 5,6-dihydroxyindoline; 5-hydroxyindole; 6-hydroxyindole; 7-hydroxyindole and 2,3-indolinedione.

5. The agent according to claim 1, wherein the persulfate salt is selected from the group consisting of potassium persulfate, sodium persulfate and ammonium persulfate.

6. The agent according to claim 1, containing the at least one hydrazone derivative of formula (I), and the at least one coupler and persulfate salt in a total amount from 0.01 to 10 weight percent, each.

7. The agent according to claim 1, containing from 0.01 to 10 weight percent of a physiologically harmless direct dye selected from the group consisting of cationic dyes, anionic dyes, disperse dyes, nitro dyes, azo dyes, quinone dyes and triphenylmethane dyes.

8. The agent according to claim 1, having a pH from 3 to 10.

9. The agent according to claim 1, consisting of a hair colorant.

10. A two-component kit consisting of a dye carrier composition, (A1) containing, at least one hydrazone derivative of formula (I) or a physiologically compatible salt thereof,

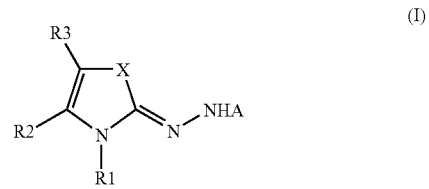

wherein

X denotes oxygen or sulfur,

A denotes hydrogen, an acetyl group, a trifluoroacetyl group, a formyl group, a ($C_1$-$C_6$)-alkylsulfonyl group or an arylsulfonyl group;

R1 denotes a saturated or unsaturated ($C_1$-$C_{12}$)-alkyl group, a halogen (F, Cl, Br, I)-substituted ($C_1$-$C_{12}$)-alkyl group, a hydroxy-($C_1$-$C_{12}$)-alkyl group, an amino-($C_1$-$C_{12}$)-alkyl group, a sulfonic acid-($C_1$-$C_{12}$)-alkyl group, a formyl group, a C(O)—($C_1$-$C_{12}$)-alkyl group, a C(O)-phenyl group, a C(O)NH—($C_1$-$C_{12}$)

alkyl group, a C(O)NH-phenyl group, a substituted or unsubstituted phenyl group or a benzyl group;

R2 and R3 can be equal or different and independently of each other denote hydrogen, a halogen atom (F, Cl, Br, I), a saturated or unsaturated $(C_1-C_{12})$-alkyl group, a halogen (F, Cl, Br, I)-substituted $(C_1-C_{12})$-alkyl group, a hydroxyl-$(C_1-C_{12})$-alkyl group, a $(C_1-C_{12})$-alkoxy group, a cyano group, a nitro group, an amino group, a $(C_1-C_{12})$-alkylamino group, a $(C_1-C_{12})$-dialkylamino group, a carboxylic acid group, a $C(O)O(C_1-C_{12})$-alkyl group, a substituted or unsubstituted C(O)O-phenyl group, a substituted or unsubstituted phenyl group or a naphthyl group;

or R2 and R3 together with the remainder of the molecule form a heterocyclic or carbocyclic, saturated or unsaturated, substituted or unsubstituted ring system;

another dye carrier composition (A2) containing couplers and persulfate salts, and optionally an agent for adjusting pH.

11. A two-component kit, containing:

a first component consisting of a powder containing at least one hydrazone derivative of formula (I) or a physiologically compatible salt thereof,

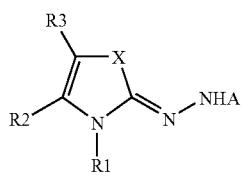

(I)

wherein

X denotes oxygen or sulfur,

A denotes hydrogen, an acetyl group, a trifluoroacetyl group, a formyl group, a $(C_1-C_6)$-alkylsulfonyl group or an arylsulfonyl group;

R1 denotes a saturated or unsaturated $(C_1-C_{12})$-alkyl group, a halogen (F, Cl, Br, I)-substituted $(C_1-C_{12})$-alkyl group, a hydroxy-$(C_1-C_{12})$-alkyl group, an amino-$(C_1-C_{12})$-alkyl group, a sulfonic acid-$(C_1-C_{12})$-alkyl group, a formyl group, a C(O)—$(C_1-C_{12})$-alkyl group, a C(O)-phenyl group, a C(O)NH—$(C_1-C_{12})$ alkyl group, a C(O)NH-phenyl group, a substituted or unsubstituted phenyl group or a benzyl group;

R2 and R3 can be equal or different and independently of each other denote hydrogen, a halogen atom (F, Cl, Br, I), a saturated or unsaturated $(C_1-C_{12})$-alkyl group, a halogen (F, Cl, Br, I)-substituted $(C_1-C_{12})$-alkyl group, a hydroxyl-$(C_1-C_{12})$-alkyl group, a $(C_1-C_{12})$-alkoxy group, a cyano group, a nitro group, an amino group, a $(C_1-C_{12})$-alkylamino group, a $(C_1-C_{12})$-dialkylamino group, a carboxylic acid group, a $C(O)O(C_1-C_{12})$-alkyl group, a substituted or unsubstituted C(O)O-phenyl group, a substituted or unsubstituted phenyl group or a naphthyl group;

or R2 and R3 together with the remainder of the molecule form a heterocyclic or carbocyclic, saturated or unsaturated, substituted or unsubstituted ring system;

the powder further consisting of couplers and the persulfate salts and optionally other common powdered cosmetic additives, and a second component consisting of water or a liquid cosmetic preparation optionally containing an agent for adjusting the pH.

12. A method for coloring hair whereby a hair colorant is applied to the hair, and after an exposure time of 5 to 60 minutes at a temperature from 20 to 50° C. the hair is rinsed with water, optionally washed with a shampoo and then dried, wherein the hair colorant comprises:

(a) at least one hydrazone derivative of formula (I) or a physiologically compatible salt thereof,

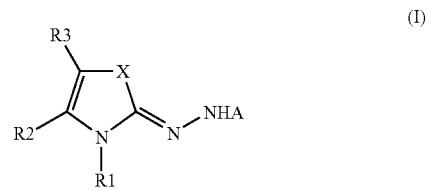

(I)

wherein

X denotes oxygen or sulfur,

A denotes hydrogen, an acetyl group, a trifluoroacetyl group, a formyl group, a $(C_1-C_6)$-alkylsulfonyl group or an arylsulfonyl group;

R1 denotes a saturated or unsaturated $(C_1-C_{12})$-alkyl group, a halogen (F, Cl, Br, I)-substituted $(C_1-C_{12})$-alkyl group, a hydroxy-$(C_1-C_{12})$-alkyl group, an amino-$(C_1-C_{12})$-alkyl group, a sulfonic acid-$(C_1-C_{12})$-alkyl group, a formyl group, a C(O)—$(C_1-C_{12})$-alkyl group, a C(O)-phenyl group, a C(O)NH—$(C_1-C_{12})$ alkyl group, a C(O)NH-phenyl group, a substituted or unsubstituted phenyl group or a benzyl group;

R2 and R3 can be equal or different and independently of each other denote hydrogen, a halogen atom (F, Cl, Br, I), a saturated or unsaturated $(C_1-C_{12})$-alkyl group, a halogen (F, Cl, Br, I)-substituted $(C_1-C_{12})$-alkyl group, a hydroxyl-$(C_1-C_{12})$-alkyl group, a $(C_1-C_{12})$-alkoxy group, a cyano group, a nitro group, an amino group, a $(C_1-C_{12})$-alkylamino group, a $(C_1-C_{12})$-dialkylamino group, a carboxylic acid group, a $C(O)O(C_1-C_{12})$-alkyl group, a substituted or unsubstituted C(O)O-phenyl group, a substituted or unsubstituted phenyl group or a naphthyl group;

or R2 and R3 together with the remainder of the molecule form a heterocyclic or carbocyclic, saturated or unsaturated, substituted or unsubstituted ring system;

(b) at least one known coupler or a physiologically compatible salt thereof; and (c) a persulfate salt as oxidant.

13. A method for coloring hair whereby the ready-for-use colorant (A) is prepared just before use by mixing a first component and second component (A1, A2)—optionally with addition of an alkalinizing agent or an acid—and is then applied to the hair, and after an exposure time of 5 to 60 minutes at a temperature from 20 to 50° C. the hair is rinsed with water, optionally washed with a shampoo and then dried, wherein the first component is a dye carrier composition (A1) containing at least one hydrazone derivative of formula (I) or a physiologically compatible salt thereof,

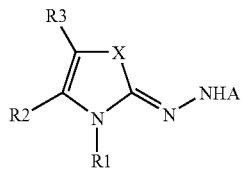
(I)

wherein

X denotes oxygen or sulfur,

A denotes hydrogen, an acetyl group, a trifluoroacetyl group, a formyl group, a ($C_1$-$C_6$)-alkylsulfonyl group or an arylsulfonyl group;

R1 denotes a saturated or unsaturated ($C_1$-$C_{12}$)-alkyl group, a halogen (F, Cl, Br, I)-substituted ($C_1$-$C_{12}$)-alkyl group, a hydroxy-($C_1$-$C_{12}$)-alkyl group, an amino-($C_1$-$C_{12}$)-alkyl group, a sulfonic acid-($C_1$-$C_{12}$)-alkyl group, a formyl group, a C(O)—($C_1$-$C_{12}$)-alkyl group, a C(O)-phenyl group, a C(O)NH—($C_1$-$C_{12}$) alkyl group, a C(O)NH-phenyl group, a substituted or unsubstituted phenyl group or a benzyl group;

R2 and R3 can be equal or different and independently of each other denote hydrogen, a halogen atom (F, Cl, Br, I), a saturated or unsaturated ($C_1$-$C_{12}$)-alkyl group, a halogen (F, Cl, Br, 1)-substituted ($C_1$-$C_{12}$)-alkyl group, a hydroxyl-($C_1$-$C_{12}$)-alkyl group, a($C_1$-$C_{12}$)-alkoxy group, a cyano group, a nitro group, an amino group, a ($C_1$-$C_{12}$)-alkylamino group, a ($C_1$-$C_{12}$)-dialkylamino group, a carboxylic acid group, a C(O)O($C_1$-$C_{12}$)-alkyl group, a substituted or unsubstituted C(O)O-phenyl group, a substituted or unsubstituted phenyl group or a naphthyl group;

or R2 and R3 together with the remainder of the molecule form a heterocyclic or carbocyclic, saturated or unsaturated, substituted or unsubstituted ring system; and wherein the second component (A2) is a further dye carrier composition containing couplers and persulfate salts, and optionally an agent for adjusting pH.

* * * * *